United States Patent [19]

Förster et al.

[11] Patent Number: 4,788,291
[45] Date of Patent: Nov. 29, 1988

[54] 4,5-DISUBSTITUTED 1,3-THIAZOL-2-YLOXYACETAMIDE HERBICIDES

[75] Inventors: Heinz Förster, Wuppertal; Gunther Beck, Leverkusen; Erich Klauke, Odenthal; Hans-Joachim Santel, Leverkusen; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 826,479

[22] Filed: Feb. 5, 1986

[30] Foreign Application Priority Data

Feb. 21, 1985 [DE] Fed. Rep. of Germany ....... 3505902

[51] Int. Cl.$^4$ ................. C07D 277/34; C07D 417/12; A01N 43/78
[52] U.S. Cl. ..................... 548/187; 546/165; 546/209; 546/256; 540/603; 71/90
[58] Field of Search ............... 540/603; 548/136, 187; 546/165, 209, 256; 71/90

[56] References Cited

U.S. PATENT DOCUMENTS

| 4,408,055 | 10/1983 | Förster et al. | 71/88 X |
| 4,465,504 | 8/1984 | Förster et al. | 71/88 |
| 4,645,525 | 2/1987 | Förster et al. | 544/138 X |

FOREIGN PATENT DOCUMENTS

| 18497 | 11/1980 | European Pat. Off. |
| 0029171 | 5/1981 | European Pat. Off. |
| 0039811 | 1/1982 | European Pat. Off. |
| 0060426 | 9/1982 | European Pat. Off. |
| 0081730 | 6/1983 | European Pat. Off. |
| 0165537 | 12/1985 | European Pat. Off. |

Primary Examiner—Donald G. Daus
Assistant Examiner—William A. Teoli, Jr.
Attorney, Agent, or Firm—Sprung Horn Kramer & Woods

[57] ABSTRACT

Herbicidally active novel 4,5-disubstituted 1,3-thiazol-2-yloxyacetamides of the formula

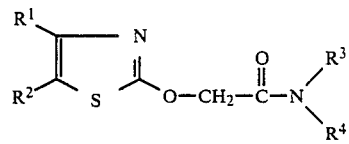

in which
$R^1$ is fluorine or chlorine,
$R^2$ is alkyl or halogenoalkyl, and
$R^3$ and $R^4$ each independently is alkyl, alkenyl, alkinyl, optionally substituted cycloalkyl, optionally substituted cycloalkenyl, halogenoalkyl, alkoxyalkyl, alkoxyalkyleneoxy, alkoxy, aralkyl or optionally substituted aryl, or
$R_3$ and $R_4$, conjointly with the nitrogen atom to which they are bonded form an optionally substituted, heterocyclic ring which can contain further hetero-atoms.

1 Claim, No Drawings

4,5-DISUBSTITUTED 1,3-THIAZOL-2-YLOXYACETAMIDE HERBICIDES

The invention relates to new 4,5-disubstituted 1,3-thiazol-2-yloxyacetamides, a process for their preparation and their use as herbicides.

It is already known that certain 4,5-disubstituted 1,3-thiazol-2-yloxyacetamides, such as, for example, 2-(4,5-dichloro-1,3-thiazol-2-yloxy)-N,N-diethylacetamide, possess herbicidal, in particular also selectively herbicidal, properties (compare, for example, EP-OS (European laid-open specification) No. 18,497).

However, the herbicidal activity of these preveiously known compounds toward weeds, as well as their selectivity toward important crop plants, is not always fully satisfactory in all use sectors.

There have been found new 4,5-disubstituted 1,3-thiazol-2-yloxyacetamides of the general formula (I)

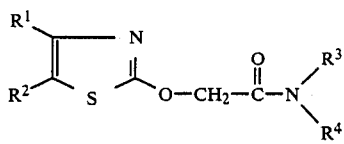

in which
$R^1$ represents fluorine or chlorine,
$R^2$ represents alkyl or halogenoalkyl and
$R^3$ and $R^4$ independently of one another represent alkyl, alkenyl, alkinyl, optionally substituted cycloalkyl or optionally substituted cycloalkenyl, halogenoalkyl, alkoxyalkyl, alkoxyalkyleneoxy or alkoxy, aralkyl or optionally substituted aryl or conjointly with the nitrogen atom to which they are bonded represent an optionally substituted, saturated or unsaturated, heterocyclic ring which can contain further hetero-atoms.

Further, it has been found that the new 4,5-disubstituted 1,3-thiazol-2-yloxyacetamides of the general formula (I) are obtained when 4,5-disubstituted 1,3-thiazoles of the formula (II)

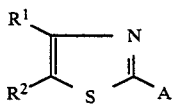

in which
$R^1$ and $R^2$ have the abovementioned meaning and
A represents an electron-attracting leaving group, are reacted with glycolic acid amides of the formula (III)

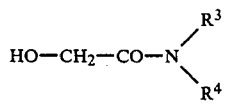

in which
$R^3$ and $R^4$ have the abovementioned meaning, if appropriate in the presence of a diluent and if appropriate in the presence of an acid acceptor as well as, if appropriate, in the presence of a catalyst.

Finally, it has been found that the new 4,5-disubstituted 1,3-thiazol-2-yloxyacetamides of the formula (I) possess herbicidal, in particular also selectively herbicidal, properties.

Surprisingly, the 4,5-disubstituted 1,3-thiazol-2-yloxyacetamides according to the invention, of the formula (I), exhibit substantially improved herbicidal activity against common weeds which are difficult to combat, and relatively good toleration by important crop plants, in comparison with the 4,5-disubstituted 1,3-thiazol-2-yloxyacetamides previously known from the state of the art, such as, for example, 2-(4,5-dichloro-1,3-thiazol-2-yloxy)-N,N-diethylacetamide which are, chemically and in respect of their action, closely related compounds.

The formula (I) provides a general definition of the 4,5-disubstituted 1,3-thiazol-2-yloxyacetamides according to the invention. Preferred compounds of the formula (I) are those in which
$R^1$ represents fluorine or chlorine,
$R^2$ represents straight-chain or branched alkyl or halogenoalkyl each with 1 to 4 carbon atoms and, where appropriate, 1 to 9 identical or different halogen atoms, such as, in particular, fluorine, chlorine or bromine and
$R^3$ and $R^4$ independently of one another represent straight-chain or branched alkyl with 1 to 8 carbon atoms, straight-chain or branched alkenyl and alkinyl each with 2 to 8 carbon atoms, cycloalkyl or cycloalkenyl, each with 3 to 7 carbon atoms, which optionally have one or more identical or different substituents (suitable substituents being, in particular, alkyl radicals with 1 to 4 carbon atoms), straight-chain or branched alkoxy, alkoxyalkyleneoxy or alkoxyalkyl each with 1 to 8 carbon atoms in the individual alkyl or alkylene moieties, halogenoalkyl with 1 to 8 carbon atoms and 1 to 5 halogen atoms, especially fluorine, chlorine and bromine, aralkyl with 6 to 10 carbon atoms in the aryl moiety and 1 to 2 carbon atoms in the alkyl moiety, as well as aryl with 6 to 10 carbon atoms which optionally has one or more identical or different substituents (possible substituents being halogen, straight-chain or branched alkyl, alkoxy or alkylthio each with 1 to 4 carbon atoms, and halogenoalkyl, halogenoalkoxy and halogenoalkylthio each with 1 to 2 carbon atoms and 1 to 5 halogen atoms, especially fluorine, chlorine and bromine, as well as nitro), or
$R^3$ and $R^4$ together with the nitrogen atom to which they are bonded represent a saturated or unsaturated, 5- to 7-membered heterocyclic ring which optionally has one or more identical or different substituents, posssible substituents being straight-chain or branched alkyl with 1 to 6 carbon atoms, also in the form of fused ring system, aryl with 6 to 10 carbon atoms, also in the form of a fused ring system, or dioxyalkylene with 2 to 3 carbon atoms.

Particularly preferred compounds of the formula (I) are those in which
$R^1$ represents fluorine or chlorine,
$R^2$ represents mehyl, trifluoromethyl, difluoromethyl, fluoromethyl, trichloromethyl, dichloromethyl, chloromethyl, fluorodichloromethyl or difluorochloromethyl and
$R^3$ and $R^4$ independently of one another represent straight-chain or branched alkyl with 1 to 6 carbon atoms, straight-chain or branched alkenyl and alkinyl each with 2 to 6 carbon atoms, cycloalkyl or cycloalkenyl with 5 to 7 carbon atoms which are optionally mono- to tri-substituted by methyl or ethyl, the substituents being identical or different, alkoxy, alkoxyalkyleneoxy or alkoxyalkyl, each of which is straight-chain or branched and has 1 to 6 carbon atoms in the individual alkyl moieties, halogenoalkyl with 1 to 6 carbon atoms and 1 to 5 halogen atoms, especially fluorine, bromine and chlorine, benzyl as well as phenyl which optionally has one to three identical or different substituents, particularly preferred substituents being methyl, ethyl, methoxy, methylthio, trifluoromethyl, trifluoromethoxy, trifluoromethylthio, fluorine, chlorine or nitro; or $R^3$ and $R^4$ together with the nitrogen atom to which they are bonded represent a heterocyclic ring of the formula

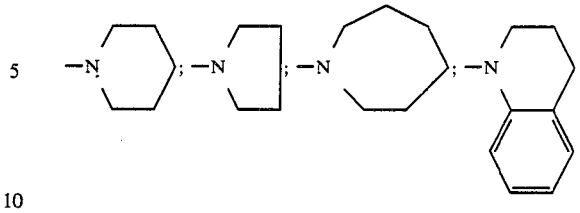

which optionally has one to three identical or different substituents, particularly preferred substituents being methyl, ethyl and phenyl.

Specifically, the following compounds of the general formula (I) may be mentioned in addition to the compounds mentioned in the preparation examples:

TABLE I $$\begin{array}{c} R^1 \\ \diagdown \\ R^2 \end{array} \!\!=\!\! \begin{array}{c} N \\ \parallel \\ S \end{array} \!\!-\!\! \overset{\parallel}{C} \!\!-\!\! O\!-\!CH_2\!-\!\overset{O}{\overset{\parallel}{C}}\!-\!N\!\!\begin{array}{c} R^3 \\ \diagdown \\ R^4 \end{array} \qquad (I)$$

| $R^1$ | $R^2$ | $R^3$ | $R^4$ | or | $-N\!\!\begin{array}{c}R^3\\ \diagdown\\ R^4\end{array}$ |
|---|---|---|---|---|---|
| Cl | $CF_3$ | $CH_3$ | $CH_3O-CH_2-$ | | |
| Cl | $CF_3$ | $CH_3$ | cyclohexyl | | |
| Cl | $CF_3$ | $CH_3$ | cyclohexenyl | | |
| Cl | $CF_3$ | $CH_3$ | $F_3C-CH_2-$ | | |
| Cl | $CF_3$ | $CH_3$ | 2-methylphenyl | | |
| Cl | $CF_3$ | $CH_3$ | 4-nitro-2-methylphenyl | | |
| Cl | $CF_3$ | $CH_3$ | 4-($F_3C$)-phenyl | | |
| Cl | $CF_3$ | $C_2H_5$ | $CH_2\!\!=\!\!CH\!-\!CH_2-$ | | |
| Cl | $CF_3$ | $CH_2\!\!=\!\!CH\!-\!CH_2-$ | $CH_2\!\!=\!\!CH\!-\!CH_2-$ | | |

TABLE I-continued $$\underset{R^2}{\overset{R^1}{\Big|}}\!\!\underset{S}{\overset{N}{=}}\!\!\overset{}{\underset{}{C}}\!\!-\!\!O\!-\!CH_2\!-\!\overset{O}{\overset{\|}{C}}\!\!-\!\!N\!\!\underset{R^4}{\overset{R^3}{\diagdown}} \qquad (I)$$

| $R^1$ | $R^2$ | $R^3$ | $R^4$ | or $-N\underset{R^4}{\overset{R^3}{\diagdown}}$ |
|---|---|---|---|---|
| Cl | $CF_3$ | | | 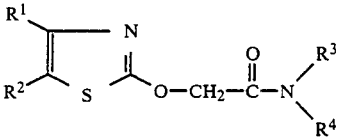 |
| Cl | $CF_3$ | | | 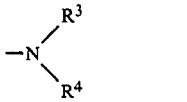 |
| Cl | $CF_3$ | | | 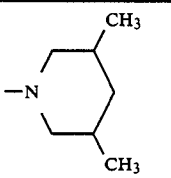 |
| Cl | $CF_3$ | | | 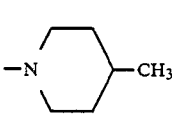 |
| Cl | $CF_3$ | $CH_3$ | $HC{\equiv}C-CH_2$ | |
| Cl | $CF_3$ | $CH_3O$ | $C_2H_5-\underset{\underset{CH_3}{\|}}{CH}-$ | |
| Cl | $CF_3$ | $(CH_3)_2CHO-$ | $C_2H_5O-CH_2CH_2-O-$ | |
| Cl | $CF_3$ | $CH_3$ | | 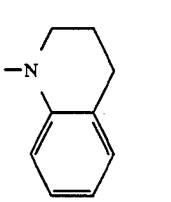 |
| Cl | $CF_3$ | $CH_3$ | | 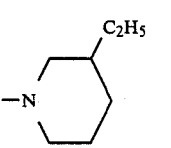 |
| Cl | $CF_3$ | $(CH_3)_2CH-$ | $(CH_3)_2CH-O-$ | |
| Cl | $CF_3$ | $C_2H_5-\underset{\underset{CH_3}{\|}}{CH}-$ | $CH_3O-CH_2-$ | |
| Cl | $CF_3$ | $CH_3(CH_2)_3-$ | $CH_3-(CH_2)_3-$ | |
| Cl | $CF_3$ | $C_2H_5-$ | $(CH_3)_2CH-$ | |
| Cl | $CF_3$ | $(CH_3)_2CH-$ | $C_2H_5OCH_2CH_2O-$ | |

TABLE I-continued $$\begin{array}{c} R^1 \\ \diagdown \\ R^2 \end{array} \diagup \begin{array}{c} N \\ \diagdown \\ S \end{array} C - O - CH_2 - \overset{O}{\underset{\parallel}{C}} - N \diagup \begin{array}{c} R^3 \\ \diagdown \\ R^4 \end{array} \quad (I)$$

| $R^1$ | $R^2$ | $R^3$ | $R^4$ | or $-N\begin{array}{c}R^3\\R^4\end{array}$ |
|---|---|---|---|---|
| Cl | CF₃ | CH₃ | | 4-Cl-C₆H₄- |
| Cl | CF₃ | CH₃ | | 4-F-C₆H₄- |
| Cl | CF₃ | CH₃ | | 3-F-C₆H₄- |
| Cl | CF₃ | | | 3-methylpiperidinyl |
| Cl | CF₃ | | | piperidinyl |
| Cl | CF₃ | | | 2-ethylpiperidinyl |
| Cl | CF₃ | | | 2-methylpiperidinyl |
| Cl | CF₃ | CH₃— | CH₂=CH—CH₂— | |
| Cl | CF₃ | CH₃— | 4-CH₃S-C₆H₄- | |
| Cl | CF₃ | CH₃— | 3-CH₃S-C₆H₄- | |
| Cl | CF₃ | CH₃— | CH₃(CH₂)₃— | |

TABLE I-continued $$\underset{R^2}{\overset{R^1}{>}}\!\!=\!\!\underset{S}{\overset{N}{\diagdown}}\!\!-\!\!O\!-\!CH_2\!-\!\underset{\|}{\overset{O}{C}}\!-\!N\!\!\underset{R^4}{\overset{R^3}{<}} \quad (I)$$

| R¹ | R² | R³ | R⁴ or $-N\!\!\underset{R^4}{\overset{R^3}{<}}$ |
|----|----|----|----|
| Cl | CF₃ | CH₃— | 4-O₂N-C₆H₄— |
| Cl | CF₃ | CH₃— | CH₂=CH— |
| Cl | CF₃ | C₂H₅— | CH₂=CH— |
| Cl | CF₃ | | 3,4-dihydro-2H-pyridin-1-yl |
| Cl | CF₃ | | 3,6-dihydro-2H-pyridin-1-yl |
| F | CF₃ | CH₃ | CH₃O—CH₂— |
| F | CF₃ | CH₃ | cyclohexyl |
| F | CF₃ | CH₃ | cyclohex-3-en-1-yl |
| F | CF₃ | CH₃ | F₃C—CH₂— |
| F | CF₃ | CH₃ | 2-methylphenyl |
| F | CF₃ | CH₃ | 4-nitro-3-methylphenyl |
| F | CF₃ | CH₃ | 4-(trifluoromethyl)phenyl |
| F | CF₃ | C₂H₅ | CH₂=CH—CH₂— |
| F | CF₃ | CH₂=CH—CH₂— | CH₂=CH—CH₂— |

TABLE I-continued $$\underset{R^2}{\overset{R^1}{>}}\!\!=\!\!\underset{S}{\overset{N}{>}}\!\!-\!\!O\!-\!CH_2\!-\!\underset{\|}{\overset{O}{C}}\!-\!N\!\!\overset{R^3}{\underset{R^4}{<}} \quad (I)$$

| $R^1$ | $R^2$ | $R^3$ | $R^4$ | or $-N\!\!\overset{R^3}{\underset{R^4}{<}}$ |
|---|---|---|---|---|
| F | $CF_3$ | | | 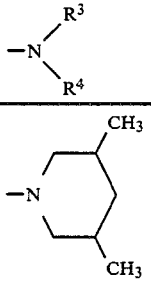 |
| F | $CF_3$ | | | 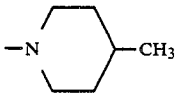 |
| F | $CF_3$ | | | 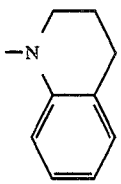 |
| F | $CF_3$ | | | 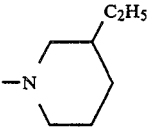 |
| F | $CF_3$ | $CH_3$ | $HC\!\equiv\!C\!-\!CH_2$ | |
| F | $CF_3$ | $CH_3O$ | $C_2H_5\!-\!\underset{\underset{CH_3}{\|}}{CH}\!-$ | |
| F | $CF_3$ | $(CH_3)_2CHO-$ | $C_2H_5O\!-\!CH_2CH_2\!-\!O-$ | |
| F | $CF_3$ | $CH_3$ | 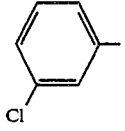 | |
| F | $CF_3$ | $CH_3$ | 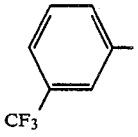 | |
| F | $CF_3$ | $(CH_3)_2CH-$ | $(CH_3)_2CH\!-\!O-$ | |
| F | $CF_3$ | $C_2H_5\!-\!\underset{\underset{CH_3}{\|}}{CH}\!-$ | $CH_3O\!-\!CH_2-$ | |
| F | $CF_3$ | $CH_3(CH_2)_3-$ | $CH_3\!-\!(CH_2)_3-$ | |
| F | $CF_3$ | $C_2H_5-$ | $(CH_3)_2CH-$ | |
| F | $CF_3$ | $(CH_3)_2CH-$ | $C_2H_5OCH_2CH_2O-$ | |

TABLE I-continued $$\underset{R^2}{\overset{R^1}{\diagdown}}\!\!=\!\!\underset{S}{\overset{N}{\diagdown}}\!\!C\!-\!O\!-\!CH_2\!-\!\overset{O}{\overset{\|}{C}}\!-\!N\!\!\overset{R^3}{\diagdown}_{R^4} \quad (I)$$

| $R^1$ | $R^2$ | $R^3$ | $R^4$ | or | $-N\!\!\overset{R^3}{\diagdown}_{R^4}$ |
|---|---|---|---|---|---|
| F | CF$_3$ | CH$_3$ | 4-Cl-C$_6$H$_4$– | | |
| F | CF$_3$ | CH$_3$ | 4-F-C$_6$H$_4$– | | |
| F | CF$_3$ | CH$_3$ | 3-F-C$_6$H$_4$– | | |
| F | CF$_3$ | | | | 3-methylpiperidino |
| F | CF$_3$ | | | | piperidino |
| F | CF$_3$ | | | | 2-ethylpiperidino |
| F | CF$_3$ | | | | 2-methylpiperidino |
| F | CF$_3$ | CH$_3$– | CH$_2$–CH–CH$_2$– | | |
| F | CF$_3$ | CH$_3$– | 4-CH$_3$S-C$_6$H$_4$– | | |
| F | CF$_3$ | CH$_3$– | 3-CH$_3$S-C$_6$H$_4$– | | |
| F | CF$_3$ | CH$_3$– | CH$_3$(CH$_2$)$_3$– | | |

TABLE I-continued
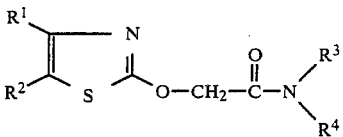
(I)
| $R^1$ | $R^2$ | $R^3$ | $R^4$ | or | $-N\begin{smallmatrix}R^3\\R^4\end{smallmatrix}$ |
|---|---|---|---|---|---|
| F | CF$_3$ | CH$_3$— | 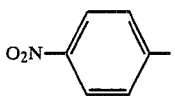 | | |
| F | CF$_3$ | CH$_3$— | CH$_2$=CH— | | |
| F | CF$_3$ | C$_2$H$_5$— | CH$_2$=CH— | | |
| F | CF$_3$ | | | | 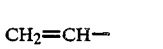 |
| F | CF$_3$ | | | | 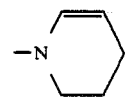 |
| F | CHF$_2$ | CH$_3$ | CH$_3$O—CH$_2$— | | |
| F | CHF$_2$ | CH$_3$ | 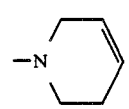 | | |
| F | CHF$_2$ | CH$_3$ | 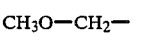 | | |
| F | CHF$_2$ | CH$_3$ | F$_3$C—CH$_2$— | | |
| F | CHF$_2$ | CH$_3$ | 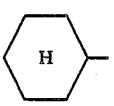 | | |
| F | CHF$_2$ | CH$_3$ | 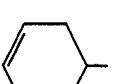 | | |
| F | CHF$_2$ | CH$_3$ | 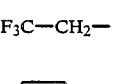 | | |
| F | CHF$_2$ | C$_2$H$_5$ | CH$_2$=CH—CH$_2$— | | |
| F | CHF$_2$ | CH$_2$=CH—CH$_2$— | CH$_2$=CH—CH$_2$— | | |

TABLE I-continued $$\underset{R^2}{\overset{R^1}{\diagup}}\!\!\!\diagdown\!\!\!\underset{S}{\diagdown}\!\!\!\diagup\!\!\!\overset{N}{\diagdown}\!\!\!\diagup\!\!\!O\!-\!CH_2\!-\!\underset{\overset{\|}{O}}{C}\!-\!N\!\underset{R^4}{\overset{R^3}{\diagdown}}\qquad (I)$$

| R¹ | R² | R³ | R⁴ | or $-N\!\!\begin{array}{c}R^3\\R^4\end{array}$ |
|---|---|---|---|---|
| F | CHF₂ | | | N-piperidinyl with 3,5-di-CH₃ |
| F | CHF₂ | | | N-piperidinyl with 4-CH₃ |
| F | CHF₂ | | | 1,2,3,4-tetrahydroquinolin-1-yl |
| F | CHF₂ | | | N-piperidinyl with 3-C₂H₅ |
| F | CHF₂ | CH₃ | HC≡C—CH₂ | |
| F | CHF₂ | CH₃O | C₂H₅—CH(CH₃)— | |
| F | CHF₂ | (CH₃)₂CHO— | C₂H₅O—CH₂CH₂—O— | |
| F | CHF₂ | CH₃ | 3-Cl-C₆H₄— | |
| F | CHF₂ | CH₃ | 3-CF₃-C₆H₄— | |
| F | CHF₂ | (CH₃)₂CH— | (CH₃)₂CH—O— | |
| F | CHF₂ | C₂H₅—CH(CH₃)— | CH₃O—CH₂— | |
| F | CHF₂ | CH₃(CH₂)₃— | CH₃—(CH₂)₃— | |
| F | CHF₂ | C₂H₅— | (CH₃)₂CH— | |
| F | CHF₂ | (CH₃)₂CH— | C₂H₅OCH₂CH₂O— | |

TABLE I-continued $$\underset{R^2}{\overset{R^1}{>}}\!\!\!\underset{S}{\underset{\|}{=}}\!\!\!\underset{}{\overset{N}{\underset{\|}{\parallel}}}\!\!\!\!C\!\!-\!\!O\!-\!\!CH_2\!\!-\!\!\underset{\|}{\overset{O}{C}}\!\!-\!\!N\!\!\underset{R^4}{\overset{R^3}{<}} \quad (I)$$

| R¹ | R² | R³ | R⁴ | or $-N{<}^{R^3}_{R^4}$ |
|---|---|---|---|---|
| F | CHF₂ | CH₃ | 4-Cl-C₆H₄- | |
| F | CHF₂ | CH₃ | 4-F-C₆H₄- | |
| F | CHF₂ | CH₃ | 3-F-C₆H₄- | |
| F | CHF₂ | | | 3-methylpiperidinyl |
| F | CHF₂ | | | piperidinyl |
| F | CHF₂ | | | 2-ethylpiperidinyl |
| F | CHF₂ | | | 2-methylpiperidinyl |
| F | CHF₂ | CH₃— | CH₂=CH—CH₂— | |
| F | CHF₂ | CH₃— | 4-(CH₃S)-C₆H₄- | |
| F | CHF₂ | CH₃— | 3-(CH₃S)-C₆H₄- | |
| F | CHF₂ | CH₃— | CH₃(CH₂)₃— | |

TABLE I-continued $$\underset{R^2}{\overset{R^1}{\diagdown}}\!\!\!\underset{S}{\diagup}\!\!\!\underset{}{\overset{N}{\diagdown}}\!\!\!\underset{}{\diagup}\!\!\!O\!\!-\!\!CH_2\!\!-\!\!\overset{O}{\overset{\|}{C}}\!\!-\!\!\underset{R^4}{\overset{R^3}{\diagdown}}\qquad(I)$$

| R¹ | R² | R³ | R⁴ | or | $-N\diagdown^{R^3}_{R^4}$ |
|---|---|---|---|---|---|
| F | CHF₂ | CH₃— | 4-O₂N-C₆H₄— | | |
| F | CHF₂ | CH₃— | CH₂=CH— | | |
| F | CHF₂ | C₂H₅— | CH₂=CH— | | |
| F | CHF₂ | | | | 3,4,5,6-tetrahydropyridin-1-yl |
| F | CHF₂ | | | | 1,2,3,6-tetrahydropyridin-1-yl |
| F | CH₂F | CH₃ | CH₃O—CH₂— | | |
| F | CH₂F | CH₃ | cyclohexyl | | |
| F | CH₂F | CH₃ | cyclohex-3-en-1-yl | | |
| F | CH₂F | CH₃ | F₃C—CH₂— | | |
| F | CH₂F | CH₃ | 2-methylphenyl | | |
| F | CH₂F | CH₃ | 3-methyl-4-nitrophenyl | | |
| F | CH₂F | CH₃ | 4-(F₃C)-C₆H₄— | | |
| F | CH₂F | C₂H₅ | CH₂=CH—CH₂— | | |
| F | CH₂F | CH₂=CH—CH₂— | CH₂=CH—CH₂— | | |

TABLE I-continued $$\underset{R^2}{\overset{R^1}{>}}\!\!=\!\!\underset{S}{\overset{N}{\diagdown}}\!\!C\!-\!O\!-\!CH_2\!-\!\underset{\|}{\overset{O}{C}}\!-\!N\!\!\diagup\!\!\underset{R^4}{\overset{R^3}{\diagdown}}\quad(I)$$

| $R^1$ | $R^2$ | $R^3$ | $R^4$ | or $-N\diagup\!\!\!\diagdown\!\!\!\underset{R^4}{\overset{R^3}{}}$ |
|---|---|---|---|---|
| F | CH₂F | | | 3,5-dimethylpiperidin-1-yl |
| F | CH₂F | | | 4-methylpiperidin-1-yl |
| F | CH₂F | | | 1,2,3,4-tetrahydroquinolin-1-yl |
| F | CH₂F | | | 3-ethylpiperidin-1-yl |
| F | CH₂F | CH₃ | HC≡C—CH₂ | |
| F | CH₂F | CH₃O | C₂H₅—CH(CH₃)— | |
| F | CH₂F | (CH₃)₂CHO— | C₂H₅O—CH₂CH₂—O— | |
| F | CH₂F | CH₃ | 3-chlorophenyl | |
| F | CH₂F | CH₃ | 3-trifluoromethylphenyl | |
| F | CH₂F | (CH₃)₂CH— | (CH₃)₂CH—O— | |
| F | CH₂F | C₂H₅—CH(CH₃)— | CH₃O—CH₂— | |
| F | CH₂F | CH₃(CH₂)₃— | CH₃—(CH₂)₃— | |
| F | CH₂F | C₂H₅— | (CH₃)₂CH— | |
| F | CH₂F | (CH₃)₂CH— | C₂H₅OCH₂CH₂O— | |

TABLE I-continued $$\underset{R^2}{\overset{R^1}{\diagdown}}C=C\underset{S}{\overset{N}{\diagdown}}C-O-CH_2-\underset{O}{\overset{O}{\underset{\parallel}{C}}}-N\underset{R^4}{\overset{R^3}{\diagdown}} \quad (I)$$

| R¹ | R² | R³ | R⁴ | or | $-N\diagdown^{R^3}_{R^4}$ |
|----|----|----|----|----|----|
| F | CH₂F | CH₃ | 4-Cl-C₆H₄- | | |
| F | CH₂F | CH₃ | 4-F-C₆H₄- | | |
| F | CH₂F | CH₃ | 3-F-C₆H₄- | | |
| F | CH₂F | | | | 3-methylpiperidin-1-yl |
| F | CH₂F | | | | piperidin-1-yl |
| F | CH₂F | | | | 2-ethylpiperidin-1-yl |
| F | CH₂F | | | | 2-methylpiperidin-1-yl |
| F | CH₂F | CH₃— | CH₂=CH—CH₂— | | |
| F | CH₂F | CH₃— | 4-(CH₃S)-C₆H₄- | | |
| F | CH₂F | CH₃— | 3-(CH₃S)-C₆H₄- | | |
| F | CH₂F | CH₃— | CH₃(CH₂)₃— | | |

TABLE I-continued $$\begin{array}{c} R^1 \\ \diagup \\ R^2 \end{array} \begin{array}{c} N \\ \diagdown \\ S \end{array} \text{O—CH}_2\text{—}\underset{\underset{\displaystyle O}{\|}}{C}\text{—N} \begin{array}{c} R^3 \\ \diagdown \\ R^4 \end{array} \quad (I)$$

| $R^1$ | $R^2$ | $R^3$ | $R^4$ | or $-N\begin{array}{c}R^3\\R^4\end{array}$ |
|---|---|---|---|---|
| F | CH₂F | CH₃— | 4-O₂N-C₆H₄— | |
| F | CH₂F | CH₃— | CH₂=CH— | |
| F | CH₂F | C₂H₅— | CH₂=CH— | |
| F | CH₂F | | | tetrahydropyridin-1-yl |
| F | CH₂F | | | tetrahydropyridin-1-yl |
| Cl | CHF₂ | CH₃ | CH₃O—CH₂— | |
| Cl | CHF₂ | CH₃ | cyclohexyl (H) | |
| Cl | CHF₂ | CH₃ | cyclohexenyl | |
| Cl | CHF₂ | CH₃ | F₃C—CH₂— | |
| Cl | CHF₂ | CH₃ | 2-CH₃-C₆H₄— | |
| Cl | CHF₂ | CH₃ | 4-O₂N-3-CH₃-C₆H₃— | |
| Cl | CHF₂ | CH₃ | 4-F₃C-C₆H₄— | |
| Cl | CHF₂ | C₂H₅ | CH₂=CH—CH₂— | |
| Cl | CHF₂ | CH₂=CH—CH₂— | CH₂=CH—CH₂— | |

TABLE I-continued $$\underset{R^2}{\overset{R^1}{\diagdown}}\!\!\!\!\!\!\!\!\!\!\!\!\!\!\!\!\!\!\!\!\!\!\!\underset{S}{\diagup}\!\!\!\!\!\!\!\!\!\!\!\!\!\!\!\!\!\!\!\!\!\underset{}{\diagdown}\!\!\!\!\underset{}{\overset{N}{\diagdown}}\!\!\!\!\!\!\!\underset{}{\diagdown}\!\!\!\!\!\!\!\text{O—CH}_2\!\!-\!\!\overset{\overset{O}{\|}}{C}\!-\!\!N\!\!\underset{R^4}{\overset{R^3}{\diagup}}$$ (I)

| $R^1$ | $R^2$ | $R^3$ | $R^4$ | or | $-N\overset{R^3}{\underset{R^4}{\diagdown}}$ |
|---|---|---|---|---|---|
| Cl | $CHF_2$ | | | | 3,5-dimethylpiperidinyl |
| Cl | $CHF_2$ | | | | 4-methylpiperidinyl |
| Cl | $CHF_2$ | | | | 1,2,3,4-tetrahydroquinolinyl |
| Cl | $CHF_2$ | | | | 3-ethylpiperidinyl |
| Cl | $CHF_2$ | $CH_3$ | $HC\equiv C-CH_2$ | | |
| Cl | $CHF_2$ | $CH_3O$ | $C_2H_5-CH(CH_3)-$ | | |
| Cl | $CHF_2$ | $(CH_3)_2CHO-$ | $C_2H_5O-CH_2CH_2-O-$ | | |
| Cl | $CHF_2$ | $CH_3$ | 3-chlorophenyl | | |
| Cl | $CHF_2$ | $CH_3$ | 3-trifluoromethylphenyl | | |
| Cl | $CHF_2$ | $(CH_3)_2CH-$ | $(CH_3)_2CH-O-$ | | |
| Cl | $CHF_2$ | $C_2H_5-CH(CH_3)-$ | $CH_3O-CH_2-$ | | |
| Cl | $CHF_2$ | $CH_3(CH_2)_3-$ | $CH_3-(CH_2)_3-$ | | |
| Cl | $CHF_2$ | $C_2H_5-$ | $(CH_3)_2CH-$ | | |
| Cl | $CHF_2$ | $(CH_3)_2CH-$ | $C_2H_5OCH_2CH_2O-$ | | |

TABLE I-continued $$\text{(I)}\quad \underset{R^2}{\overset{R^1}{>}}\!\!=\!\!\underset{S}{\overset{N}{>}}\!\!-\!\!O-CH_2-\overset{O}{\overset{\|}{C}}-N\underset{R^4}{\overset{R^3}{<}}$$

| $R^1$ | $R^2$ | $R^3$ | $R^4$ | or $-N\underset{R^4}{\overset{R^3}{<}}$ |
|---|---|---|---|---|
| Cl | CHF$_2$ | CH$_3$ | 4-Cl-C$_6$H$_4$- | |
| Cl | CHF$_2$ | CH$_3$ | 4-F-C$_6$H$_4$- | |
| Cl | CHF$_2$ | CH$_3$ | 3-F-C$_6$H$_4$- | |
| Cl | CHF$_2$ | | | 3-methylpiperidin-1-yl |
| Cl | CHF$_2$ | | | piperidin-1-yl |
| Cl | CHF$_2$ | | | 2-ethylpiperidin-1-yl |
| Cl | CHF$_2$ | | | 2-methylpiperidin-1-yl |
| Cl | CHF$_2$ | CH$_3$- | CH$_2$=CH—CH$_2$- | |
| Cl | CHF$_2$ | CH$_3$- | 4-(CH$_3$S)-C$_6$H$_4$- | |
| Cl | CHF$_2$ | CH$_3$- | 3-(CH$_3$S)-C$_6$H$_4$- | |
| Cl | CHF$_2$ | CH$_3$- | CH$_3$(CH$_2$)$_3$- | |

TABLE I-continued

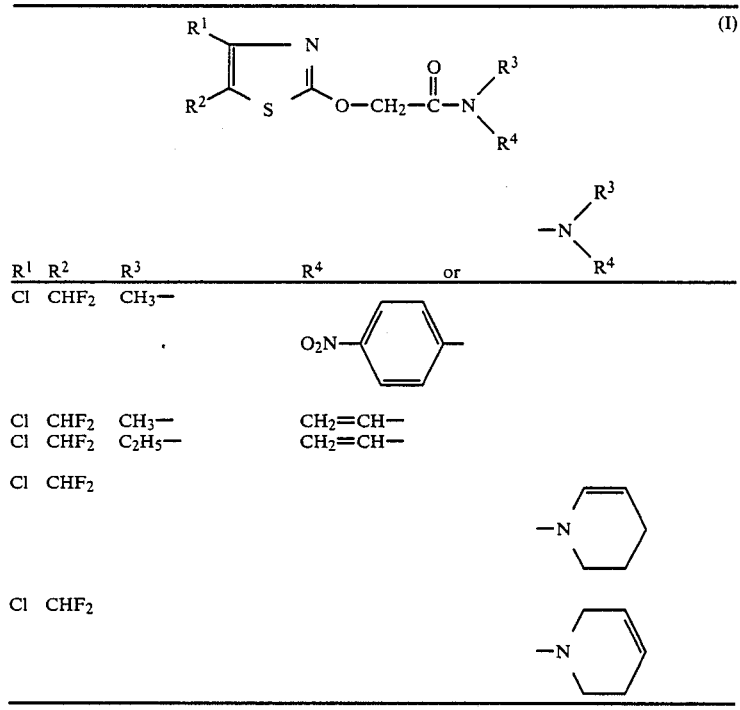

| R¹ | R² | R³ | R⁴ | or | $-N\begin{smallmatrix}R^3\\R^4\end{smallmatrix}$ |
|----|----|----|----|----|----|
| Cl | CHF₂ | CH₃— | O₂N—C₆H₄— | | |
| Cl | CHF₂ | CH₃— | CH₂=CH— | | |
| Cl | CHF₂ | C₂H₅— | CH₂=CH— | | |
| Cl | CHF₂ | | | | —N(tetrahydropyridyl) |
| Cl | CHF₂ | | | | —N(dihydropyridyl) |

If, for example, 2-chloro-4-fluoro-5-trifluoromethyl-1,3-thiazole and glycolic acid N-methylanilide are used as starting materials, the course of the reaction of the process according to the invention can be represented by the following equation:

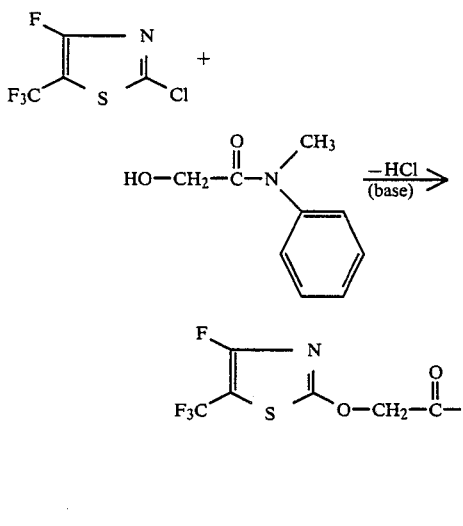

The formula (II) provides a general definition of the 4,5-disubstituted 1,3-thiazoles required as starting materials for carrying out the process according to the invention. Preferred compounds of the formula (II) are those in which R¹ and R² represent those radicals which have already been mentioned, in connection with the description of the compounds according to the invention, of the formula (I), as being preferred for these substituents; A preferably represents halogen, especially chlorine or fluorine.

The 4,5-disubstituted 1,3-thiazoles of the formula (II) were not previously known (an exception is 2,4-dichloro-5-trifluoromethyl-1,3-thiazole, compare J. Heterocycl. Chem. 13, 1297–1304 (1976), which had not however previously been isolated).

4,5-Disubstituted 1,3-thiazoles of the formula (IIa)

$$\underset{R^{2'}}{\overset{R^{1'}}{\diagup}}\!\!\!\!\!\diagdown_{S}\!\!\!\diagup\!\!\!\diagdown_{A'}^{N} \qquad \text{(IIa)}$$

which were not previously known and
in which
A', R¹' and R²' have the same meaning as the above-mentioned substituents A, R¹ and R², but A' and R¹' do not simultaneously represent chlorine if R²' represents trifluoromethyl,
are obtained when thiazolidine-diones of the formula (IV)

$$\underset{R^{2''}}{\overset{O}{\diagdown}}\!\!\!\!\!\diagup_{S}\!\!\!\diagdown_{O}^{NH} \qquad \text{(IV)}$$

in which
R²'' represents alkyl, especially methyl, are reacted with phosphorus oxychloride, if appropriate in the presence of a catalyst, such as, for example, N,N-dimethylformamide, at temperatures between +50° C. and +120° C. and, where appropriate, in a 2nd stage the 2,4-dichloro-1,3-thiazoles thus obtained, of the formula (IIb)

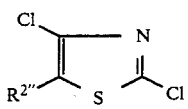

(IIb)

in which

R[2]″ has the abovementioned meaning, are reacted with chlorine, if appropriate in the presence of a diluent, such as, for example, carbon tetrachloride or phosphorus oxychloride, at temperatures between 50° C. and 250° C. and, if appropriate, in a 3rd stage the 5-chloroalkyl-2,4-dichloro-1,3-thiazoles thus obtainable, of the formula (IIc)

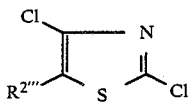

(IIc)

in which

R[2]‴ represents chloroalkyl, especially chloromethyl, dichloromethyl or trichloromethyl, are fluorinated with hydrofluoric acid or an alkali metal fluoride such as, for example, potassium fluoride, if appropriate in the presence of a diluent, such as, for example, tetramethylenesulphone, if appropriate under pressure, at temperatures between +40° C. and +200° C.

The thiazolidine-diones of the formula (IV) are known (compare, for example, J. prakt. Chemie (2) 123, 114–121 (1931)) or can be prepared in analogy to known processes.

The formula (III) provides a general definition of the glycolic acid amides furthermore required as starting materials for carrying out the process according to the invention. In this formula (III), R[3] and R[4] preferably represent those radicals which have already been mentioned as being preferred for these substituents in the description of the compounds according to the invention, of the formula (I). The glycolic acid amides of the formula (III) are also known (compare, for example, DE-OS (German published specification) No. 2,904,490, EP-OS (European published specification) No. 5,501, EP-OS (European published specification) No. 29,171, DE-OS (German published specification) No. 3,038,598 and DE-OS (German published specification) No. 3,244,956).

Possible diluents for the process according to the invention are organic or inorganic solvents. Preferred diluents are hydrocarbons, such as toluene or cyclohexane, halogenohydrocarbons, such as methylene chloride, chloroform, dichloroethane or chlorobenzene, ketones, such as acetone or methyl isobutyl ketone, ethers, such as diethyl ether, diisopropyl ether or methyl t-butyl ether, alcohols, such as methanol, ethanol or isopropanol, amides, such as dimethylformamide or dimethylacetamide, sulphoxides, such as dimethylsulphoxide, water or aqueous salt solutions.

The salts used are preferably chlorides or sulphates of alkali metals or alkaline earth metals, such as, for example, sodium chloride, potassium chloride or calcium chloride. Sodium chloride is particularly preferred.

The process according to the invention is advantageously carried out using acid acceptors. As such, strongly basic alkali metal and alkaline earth metal compounds, for example oxides, such as, for example, sodium, potassium, magnesium and calcium oxide, hydroxides, such as, for example, sodium, potassium, magnesium and calcium hydroxide and/or carbonate, such as, for example, sodium, potassium, magnesium and calcium carbonate, are preferably used.

The addition of 0.01 to 10% by weight (based on glycolic acid amide employed, of the formula (III)) of a phase transfer catalyst may prove advantageous in some cases. As examples of such catalysts there may be mentioned.

Tetrabutylammonium chloride, tetrabutylammonium bromide, tributyl-methylphosphonium bromide, trimethyl-$C_{13}/C_{15}$-alkyl-ammonium chloride, dibenzyl-dimethylammonium methylsulphate, dimethyl-$C_{12}/C_{14}$-alkyl-benzylammonium chloride, tetrabutylammonium hydroxide, 18-crown-6, triethylbenzylammonium chloride, trimethylbenzylammonium chloride and tetraethylammonium bromide.

In the process acccording to the invention, the reaction temperatures can be varied within a substantial range. They are in general between −50° C. and +100° C., preferably between −20° C. and +100° C.

The process according to the invention is in general carried out under normal pressure but can also be carried out under elevated or reduced pressure, approximately between 0.1 and 10 bar.

To carry out the process according to the invention, in general 0.1 to 10 moles, preferably 0.8 to 1.2 moles, of glycolic acid amide of the formula (III) and 0.5 to 10 moles, preferably 0.5 to 3 moles, of base are employed per mole of 4,5-disubstituted 1,3-thiazole of the formula (II). The sequence of addition of the reactants can be varied as desired, and it is also possible to introduce all components simultaneously into the reaction vessel. The reaction can be carried out continuously or discontinuously. Working up is carried out in the usual manner.

The active compounds according to the invention can be used as defoliants, desiccants, agents for destroying broad-leaved plants and, in particular, weed-killers. By weeds in the broadest sense there are to be understood all plants which grow in locations where they are undesired. Whether the compounds according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopercurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings, and hopfields, and for the selective combating of weeds in annual cultures.

In addition to an excellent action against weeds, the active compounds according to the invention also show good toleration by important crop plants and can therefore be employed as selective agents for combating weeds in dicotyledon crops, such as soy beans, cotton, sugar beet and others.

In addition, the active compounds according to the invention, when used in appropriate amounts, also exhibit a powerful fungicidal and plant-growth regulating action.

The active compounds according to the invention can be employed with particularly good success for combating diseases of rice, such as, for example, the pathogen of rice blast disease (Pyricularia oryzae).

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for use on seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can for example also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable for example ground natural minerals, such as kaolins, clays, talc, chalk, quartz, attapulgite, montmorillonite or diatomaceous earth, and ground synthetic minerals such as highly dispersed silicic acid, alumina and silicates; as solid carriers for granules there are suitable for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates, as well as albumin hydrolysis products; as dispersing agents there are suitable for example lignin-sulphite waste liquors and methylcellulose.

Adhesives, such as carboxymethylcellulose and natural and synthetic polymers in the form of powders, granules or latices can be used in the formulations, such as gum arabic, polyvinyl alcohol, polyvinyl acetate as well as natural phospholipids, such as cephalins and lecithins, and synthetic phospholipids. Further possible additives include mineral oils and vegetable oils.

It is possible to use colorants such as inorganic pigments, for example iron oxide, titanium oxide and Prussian Blue, and organic dyestuffs, such as alizarin, azo and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90% by weight.

When used as herbicides, the active compounds according to the invention, as such or in the form of their formulations, can also be used, for combating weeds, as mixtures with known herbicides, finished formulations or tank mixing being possible.

In the mixtures it is possible to use known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethyl-urea for combating weeds in cereals; 4-amino-3-methyl-6-phenyl-1,2,4-triazin-5(4H)-one for combating weeds in sugar beet and 4-amino-6-(1,2-dimethylethyl)-3-methylthio-1,2,4-triazin-5(4H)-one for combating weeds in soy beans. Mixtures with N,N-dimethyl-N'-(trifluoromethylphenyl)-urea, chloroacetic acid N-(methoxymethyl)-2,6-diethylanilide, 2-ethyl-6-methyl-N-(1-methyl-2-methoxyethyl)-chloroacetanilide; 2,6-dinitro-4-trifluoromethyl-N,N-dipropylaniline; 5-amino-4-chloro-2-phenyl-2,3-dihydro-3-oxo-pyridazine; N,N-diisopropyl-S-(2,3,3-trichloroallyl)-thiolcarbamate; 2-ethoxy-2,3-dihydro-3,3-dimethyl-5-benzofuranyl-methanesulphonate; 1-isobutylaminocarbonyl-2-imidazolidinone; N-cyclohexyl-N,S-diethyl-thiolcarbamate; 3-cyclohexyl-5,6-trimethyleneuracil, with other heteroaryloxyacetamides or aryl- or heteroaryloxy-phenoxy-propionic acids can also be used. Some mixtures surprisingly also show a synergistic action.

Mixtures with other known active compounds, such as fungicides, insecticides, acaricides, nematicides, bird repellents, plant nutrients and agents which improve soil structure are also possible.

The active compounds can be used as such, as their formulations or as the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied both before and after emergence of the plants. They can also be incorporated into the soil before sowing.

The amount of active compound used can vary within a substantial range. It depends essentially on the nature of the desired effect. In general, the amounts used for application as herbicides are between 0.01 and 10 kg of active compound per hectare of soil surface, preferably between 0.05 and 5 kg per hectare.

The examples which follow serve further to explain the invention.

PREPARATION EXAMPLES

Example 1

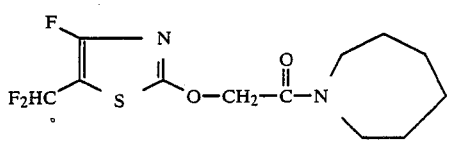

8.5 g (0.05 mol) of 2-chloro-4-fluoro-5-difluoromethyl-1,3-thiazole in 10 ml of acetonitrile are slowly added dropwise, with stirring, to 7.9 g (0.05 mol) of hydroxyacetic acid N,N-hexamethylenimide and 3.1 g (0.05 mol) of potassium hydroxide in 100 ml of isopropanol at $-20°$ C. and after completion of the addition the mixture is stirred for a further 12 hours at $-20°$ C. When the starting product is no longer detectable in the thin-layer chromatogram, the reaction mixture is poured into water and the crystalline product is filtered off and rinsed with water and a small amount of cold ligroin. 12 g (80% of theory) of 2-(4-fluoro-5-difluoromethyl-thiazol-2-yloxy)acetic acid N,N-hexamethylenimide of melting point 66° C. are obtained.

Proceeding analogously, and in accordance with the general preparation statements, the following compounds of the general formula (I)-compare Table 2- are obtained:

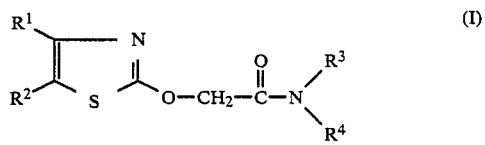

(if the substances are obtained as oils, they are isolated, in the generally customary manner, by extraction from the aqueous mixture, using an organic solvent).

TABLE 2

| Example No. | $R^1$ | $R^2$ | $-N{\overset{R^3}{\underset{R^4}{}}}$ | Physical data |
|---|---|---|---|---|
| 2 | Cl | $CH_3$ | −N(hexamethylenimide ring) | M.p.: 61° C. |
| 3 | Cl | $CH_3$ | $-N(C_2H_5)(C_2H_5)$ | M.p.: 42° C. |
| 4 | Cl | $CH_3$ | $-N(CH_3)(C_6H_5)$ | M.p.: 82° C. |
| 5 | Cl | $CHCl_2$ | $-N(CH_3)(C_6H_5)$ | M.p.: 94° C. |
| 6 | Cl | $CF_2Cl$ | $-N(CH_3)(C_6H_5)$ | M.p.: 84° C. |
| 7 | Cl | $CF_2Cl$ | $-N(C_2H_5)(C_2H_5)$ | $n_D^{20} = 1.5060$ |
| 8 | Cl | $CF_2Cl$ | $-N(OCH_3)(CH(CH_3)C_2H_5)$ | $n_D^{20} = 1.4950$ |
| 9 | Cl | $CHF_2$ | $-N(O-CH_2CH_2OC_2H_5)(CH(CH_3)_2)$ | $n_D^{20} = 1.4891$ |
| 10 | Cl | $CHF_2$ | $-N(C_2H_5)(C_2H_5)$ | M.p.: 64° C. |
| 11 | Cl | $CHF_2$ | −N(hexamethylenimide ring) | M.p.: 72° C. |
| 12 | F | $CHF_2$ | $-N(CH_3)(C_6H_5)$ | M.p.: 78° C. |
| 13 | F | $CHF_2$ | $-N(C_2H_5)(C_2H_5)$ | M.p.: 50° C. |
| 14 | Cl | $CHF_2$ | $-N(CH_3)(C_6H_5)$ | M.p.: 74° C. |

TABLE 2-continued

| Example No. | R¹ | R² | -N(R³)(R⁴) | Physical data |
|---|---|---|---|---|
| 15 | Cl | CF₃ | -N(CH₃)(C₆H₅) | M.p.: 115° C. |
| 16 | Cl | CF₃ | -N(hexamethyleneimino, 7-membered ring) | M.p.: 70° C. |
| 17 | Cl | CF₃ | -N(C₂H₅)(C₂H₅) | M.p.: 39° C. |
| 18 | Cl | CF₃ | -N(CH₂-CH=CH₂)(CH₂-CH=CH₂) | M.p.: 66° C. |
| 19 | Cl | CF₃ | -N(CH₃)(CH₃) | M.p.: 58° C. |
| 20 | Cl | CF₃ | -N(4-methylpiperidino) | M.p.: 72° C. |
| 21 | Cl | CF₃ | -N(3-methylpiperidino) | $n_D^{20} = 1.4908$ |
| 22 | Cl | CF₃ | -N(3,5-dimethylpiperidino) | $n_D^{20} = 1.4965$ |
| 23 | Cl | CF₃ | -N((CH₂)₂-CH₃)((CH₂)₂-CH₃) | $n_D^{20} = 1.4774$ |
| 24 | Cl | CF₃ | -N(OCH₃)(CH(CH₃)-C₂H₅) | $n_D^{20} = 1.4715$ |
| 25 | Cl | CF₃ | -N(O-CH₂CH₂OC₂H₅)(CH(CH₃)₂) | $n_D^{20} = 1.5664$ |
| 26 | F | CHF₂ | -N(OCH₂CH₂OC₂H₅)(CH(CH₃)₂) | M.p.: 54–56° C. |
| 27 | F | CHF₂ | -N(OCH₃)(CH(CH₃)-C₂H₅) | $n_D^{20} = 1.4715$ |
| 28 | F | CHF₂ | -N((CH₂)₂-CH₃)((CH₂)₂-CH₃) | $n_D^{20} = 1.4799$ |
| 29 | Cl | CF₃ | -N((CH₂)₃-CH₃)((CH₂)₃-CH₃) | $n_D^{20} = 1.4741$ |
| 30 | Cl | CF₃ | -N(1,2,3,4-tetrahydroquinolin-1-yl) | M.p.: 60° C. |
| 31 | F | CF₃ | -N(CH₃)(C₆H₅) | M.p.: 54° C. |
| 32 | F | CF₃ | -N(CH(CH₃)₂)(O-CH₂-CH₂-OC₂H₅) | $n_D^{20} = 1.5953$ |

PREPARATION OF THE STARTING COMPOUNDS

Example II-1

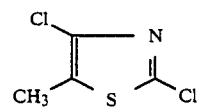

A mixture of 750 ml of phosphorus oxychloride, 157.2 g (1.2 mols) of 5-methyl-2,4-thiazolidinedione and 4 ml of dimethylformamide is heated under reflux, with stirring, until gas evolution has virtually ceased (about 6 hours). The reaction mixture, when it has cooled, is subsequently poured out, a little at a time, onto 5 kg of ice, with good stirring. It is then extracted by shaking three times with about 1 liter of methylene chloride at a time, the methylene chloride is distilled off in vacuo and the residue (187.3 g) is distilled. At 86° C./18 mbar, 159.1 g (78.9% of theory) of 2,4-dichloro-5-methylthiazole (in a purity of 99.9%, determined by gas chromatography), of boiling point 203° C. (at atmospheric pressure), are obtained.

Example II-2

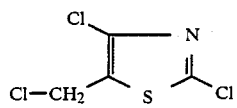

205 g (1.22 mols) of 2,4-dichloro-5-methylthiazole are chlorinated in a chlorination apparatus (compare DE-OS (German published specification) No. 2,844,270, pages 18 and 23), at the boil (temperature in the reaction vessel initially 205° C.), under UV irradiation from an Hg high pressure lamp. As soon as the temperature in the reactor has reached 235° C., the chlorination is stopped. Conversion about 80%. According to analysis by gas chromatography, the chlorination mixture has the following composition:

19.5% of 2,4-dichloro-5-methylthiazole
79.0% of 5-chloromethyl-2,4-dichlorothiazole
1.5% of 2,4-dichloro-5-(dichloromethyl)-thiazole.

Fractional distillation using a packed column of 30 cm effective length, packed with glass rings of 2 mm diameter and 2 mm length, gives, at a boiling point of 118°-119° C./20 mbar, 145 g (72% of theory, based on conversion) of 5-chloromethyl-2,4-dichlorothiazole, having a refractive index $n_D^{20} = 1.5835$; purity, according to gas chromatography: 98.5%.

Example II-3

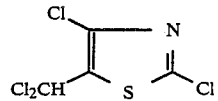

100 g (1.41 mols) of chlorine are passed into a mixture of 59 g (0.35 mol) of 2,4-dichloro-5-methylthiazole and 450 ml of tetrachloromethane in the course of 6 hours at the reflux temperature (about 80° C.). According to analysis by gas chromatography, the reaction mixture consists of:

2.0% of 5-chloromethyl-2,4-dichlorothiazole
89.4% of 2,4-dichloro-5-(dichloromethyl)-thiazole
7.9% of 2,4-dichloro-5-(trichloromethyl)-thiazole Fractional distillation using a packed column of about 30 cm length gives, as the main runnings at boiling point 122°-125° C./20 mbar, 48.5 g of 2,4-dichloro-5-(dichloromethyl)-thiazole, in a purity, determined by gas chromatography, of 94.0%. Yield (based on 100% pure product): 54.8% of theory.

Example II-4

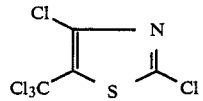

340 g of chlorine are passed into 1,008 g (6 mols) of 2,4-dichloro-5-methylthiazole dissolved in 600 ml of tetrachloromethane over the course of 6 hours at 200°-210° C., and thereafter a further 860 g of chlorine (making a total of 1,200 g = 16.9 mols) are passed in over the course of 7 hours at between 210° and 240° C. The gas chromatogram of the crude mixture shows that of the four possible 2,4-dichlorothiazoles (5-methyl-, 5-chloromethyl-, 5-dichloromethyl- and 5-trichloromethyl-), only 2,4-dichloro-5-(trichloromethyl)-thiazole is present. Working up by distillation gives, at 136°-137° C./19 mbar, 773 g (49.1% of theory, based on the amount of chlorine employed) of 2,4-dichloro-5-(trichloromethyl)-thiazole. Purity according to gas chromatography: 97.1%.

Example II-5

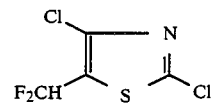

430 g (1.8 mols) of 2,4-dichloro-5-dichloromethyl-1,3-thiazole are fluorinated with 650 ml of anhydrous hydrogen fluoride in a stainless steel autoclave at 137°-140° C./18-22 bar. The hydrogen chloride formed is released continuously. After completion of the reaction, the excess hydrogen fluoride is stripped off in vacuo at room temperature, the residue is poured onto ice water and taken up in methylene chloride, and the methylene chloride solution is dried over sodium sulphate and distilled. 275 g (74.3% of theory) of 2,4-dichloro-5-difluoromethyl-1,3-thiazole are obtained, boiling point at 12 mbar/65°-66° C.; $n^{20} = 1.5070$, together with 30 g of more highly fluorinated constituents.

Examples II-6 and II-7

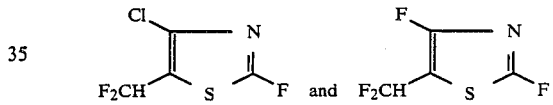

230 g (1.12 mols) of 2,4-dichloro-5-difluoromethyl-1,3-thiazole are stirred with 131 g (2.25 mols) of potassium fluoride in 339 ml of tetramethylenesulphone for 3 hours at 160° C. The fluorinated product is then distilled off in vacuo until the boiling point of the tetramethylene sulphone is reached.

Redistillation gives:

76 g (40% of theory) of 2,4-difluoro-5-difluoromethyl-1,3-thiazole of boiling point 108°-9° C.; refractive index $n_D^{20} = 1.4108$ and 47 g (22.4% of theory) of 2-fluoro-4-chloro-5-difluoromethyl-1,3-thiazole of boiling point 141°-3° C.; refractive index $n_D^{20} = 1.4528$, as well as 40 g of starting compound.

Examples II-8 and II-9

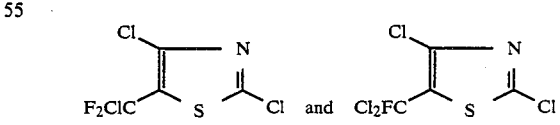

227 g (0.836 mol) of 2,4-dichloro-5-trichloromethyl-1,3-thiazole are fluorinated with 200 ml of anhydrous hydrogen fluoride in a stainless steel autoclave at 50° C./3-8 bar. The hydrogen chloride formed is released continuously. After completion of the reaction (about 4 hours), the mixture is cooled to room temperature and the excess hydrogen fluoride is stripped off in vacuo down to 100 mbar. The residue is poured onto ice water and taken up in methylene chloride, and the methylene chloride solution is dried over sodium sulphate and distilled.

84 g (39.5% of theory) of 2,4-dichloro-5-difluoro-chloromethyl-1,3-thiazole of boiling point 76°–8° C./18 mbar; refractive index $n_D^{20}=1.5120$, and 67 g (33.7% of theory) of 2,4-dichloro-5-dichloro-fluoromethyl-1,3-thiazole of boiling point 105°–107° C./18 mbar; refractive index $n_D^{20}=1.5539$ as well as 12 g of starting compound, are obtained.

If the reaction is carried out at 60° C./5 bar, 2,4-dichloro-5-difluorochloromethyl-1,3-thiazole is obtained in a yield of 71% of theory.

Example II-10

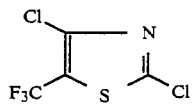

500 g (1.84 mols) of 2,4-dichloro-5-trichloromethyl-1,3-thiazole are fluorinated with 740 ml of anhydrous hydrogen fluoride in a stainless steel autoclave at 120°–140° C./25–30 bar for 3 hours. The hydrogen chloride formed is released continuously. After completion of the reaction, the mixture is cooled and the excess hydrogen fluoride is stripped off in a water pump vacuum down to 100 mbar. The residue is poured onto ice water and taken up in methylene chloride, and the methylene chloride solution is dried over sodium sulphate and distilled.

280 g (68.5% of theory) of 2,4-dichloro-5-trifluoromethyl-1,3-thiazole of boiling point 50° C./16 mbar; refractive index $n_D^{20}=1.4710$, and 63 g of partially fluorinated compounds, are obtained.

Use examples

In the use example which follows, the compound shown below was employed as the comparison substance:

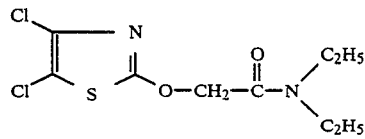

2-(4,5-dichloro-1,3-thiazol-2-yloxy)-N,N-diethyl-acetamide (known from EP-OS (European published specification) No. 18,497).

Example A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After 3 weeks, the degree of damage to the plants is rated in % damage in comparison to the development of the untreated control. The figures denote:

0%=no action (like untreated control)
100%=total destruction

Distinct superiority in herbicidal activity, with comparable crop plant selectivity, relative to the state of the art are shown in this test by, for instance, the compounds according to the following preparation examples: 12, 14, 15, 16, 17, 24 and 25.

It will be understood that the specification and examples are illustrative but not limitative of the present invention and that other embodiments within the spirit and scope of the invention will suggest themselves to those skilled in the art.

What is claimed:

1. A compound, wherein such compound is 2-(4-chloro-5-difluoromethylthiazol-2-yloxy)-acetic acid N-methyl-anilide of the formula

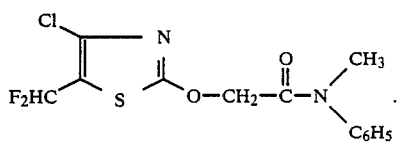

* * * * *